United States Patent
Lian et al.

(10) Patent No.: US 8,394,029 B2
(45) Date of Patent: Mar. 12, 2013

(54) NIGHT RESPIRATION RATE FOR HEART FAILURE MONITORING

(75) Inventors: Jie Lian, Beaverton, OR (US); Sharon Lefkov, Portland, OR (US); Dirk Muessig, West Linn, OR (US); Christopher S. de Voir, Tigard, OR (US); Michael V. Orlov, Brookline, MA (US)

(73) Assignee: Biotronik CRM Patent AG, Baar (CH)

( * ) Notice: Subject to any disclaimer, the term of this patent is extended or adjusted under 35 U.S.C. 154(b) by 954 days.

(21) Appl. No.: 12/476,164

(22) Filed: Jun. 1, 2009

(65) Prior Publication Data
US 2009/0312649 A1  Dec. 17, 2009

Related U.S. Application Data

(60) Provisional application No. 61/073,044, filed on Jun. 17, 2008.

(51) Int. Cl.
*A61B 5/08* (2006.01)
(52) U.S. Cl. .................. 600/484; 600/509; 600/536
(58) Field of Classification Search .............. 600/483, 600/484, 508, 529, 532, 301
See application file for complete search history.

(56) References Cited

U.S. PATENT DOCUMENTS

| | | | |
|---|---|---|---|
| 5,562,711 A * | 10/1996 | Yerich et al. ............... 607/17 |
| 6,752,765 B1 * | 6/2004 | Strobel et al. ............. 600/536 |
| 7,887,493 B2 * | 2/2011 | Stahmann et al. .......... 600/529 |
| 2004/0127804 A1 * | 7/2004 | Hatlesad et al. ........... 600/513 |
| 2005/0080460 A1 * | 4/2005 | Wang et al. ................ 607/17 |
| 2007/0118054 A1 * | 5/2007 | Pinhas et al. .............. 600/587 |
| 2007/0135725 A1 * | 6/2007 | Hatlestad .................. 600/529 |
| 2007/0173728 A1 * | 7/2007 | Pu et al. .................... 600/484 |
| 2008/0157980 A1 * | 7/2008 | Sachanandani et al. ... 340/573.1 |
| 2008/0312541 A1 * | 12/2008 | Lewicke et al. ........... 600/484 |
| 2009/0076397 A1 * | 3/2009 | Libbus et al. ............. 600/484 |

FOREIGN PATENT DOCUMENTS

EP 1 177 764   2/2002
WO WO 2007/064682   6/2007

OTHER PUBLICATIONS

European Search Report, dated Sep. 4, 2009.

* cited by examiner

*Primary Examiner* — Charles A Marmor, II
*Assistant Examiner* — Eileen Foley
(74) *Attorney, Agent, or Firm* — ARC IP Law, PC; Joseph J. Mayo

(57) ABSTRACT

The invention refers to a monitoring device for monitoring and analyzing physiological signals. The monitoring device comprises a transthoracic impedance measurement unit and an evaluation unit connected to the transthoracic impedance measurement unit. The transthoracic impedance measurement unit is adapted to conduct a transthoracic impedance measurement and to generate a transthoracic impedance signal representing a measured transthoracic impedance at consecutive points in time. The evaluation unit being configured to process the transthoracic impedance signal received from the transthoracic impedance measurement unit and to thus generate a respiration signal and to generate therefrom an evaluation signal reflecting at least a diurnal pattern of the respiration rate.

15 Claims, 4 Drawing Sheets

Intrathoracic Impendance Configurations

RV based

LV based

NIGHT RESPIRATION RATE FOR HEART FAILURE MONITORING

This application takes priority from U.S. Provisional Patent Application Ser. No. 61/073,044, filed 17 Jun. 2008, the specification of which is hereby incorporated herein by reference.

BACKGROUND OF THE INVENTION

Field of the Invention

The present invention generally relates to implantable cardiac devices, including pacemakers, defibrillators and cardioverters, which monitor the cardiac status and stimulate cardiac tissue electrically to control the patient's heart rhythm. More particularly, the present invention relates to a method and apparatus for monitoring heart failure status by trending analysis of circadian pattern of respiration rate, resting heart rate, and heart rate variability.

BRIEF SUMMARY OF THE INVENTION

According to this invention, monitoring the heart failure status is accomplished by trending analysis of multiple physiological parameters of the patient, including at least the diurnal pattern of the respiration rate, which is measured by means of transthoracic impedance of the implantable cardiac device.

In a preferred embodiment, early detection of heart failure or decompensation is made when the implantable cardiac device detects an increase of the night respiration rate of the patient, and/or decrease of the daytime respiration rate of the patient, and/or decrease of the circadian variability of the respiration rate of the patient. Alternatively, heart failure monitoring is achieved by trending analysis of multiple physiological parameters, including but are not limited to, the respiration rate, the heart rate, and the heart rate variability.

No additional leads or sensors are required beyond those for known implantable cardiac devices. The impedance measurements can be made with customary pacing/defibrillation leads, including leads placed endocardially, epicardially, or thru the coronary sinus. The information can become part of a medical information system, which provides early warning for detecting decompensating ventricular function, response to therapeutic intervention or developing heart failure.

Present invention identifies underlying physiologic changes that are latent in typical measures (electrogram) associated with left ventricular failure or its resolution. Circadian variation of respiration rate (including night respiratory rate) provides a novel probe of autonomic nervous function, and is particularly useful for heart failure monitoring.

The details of the invention can be understood from the following drawings and the corresponding text descriptions.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
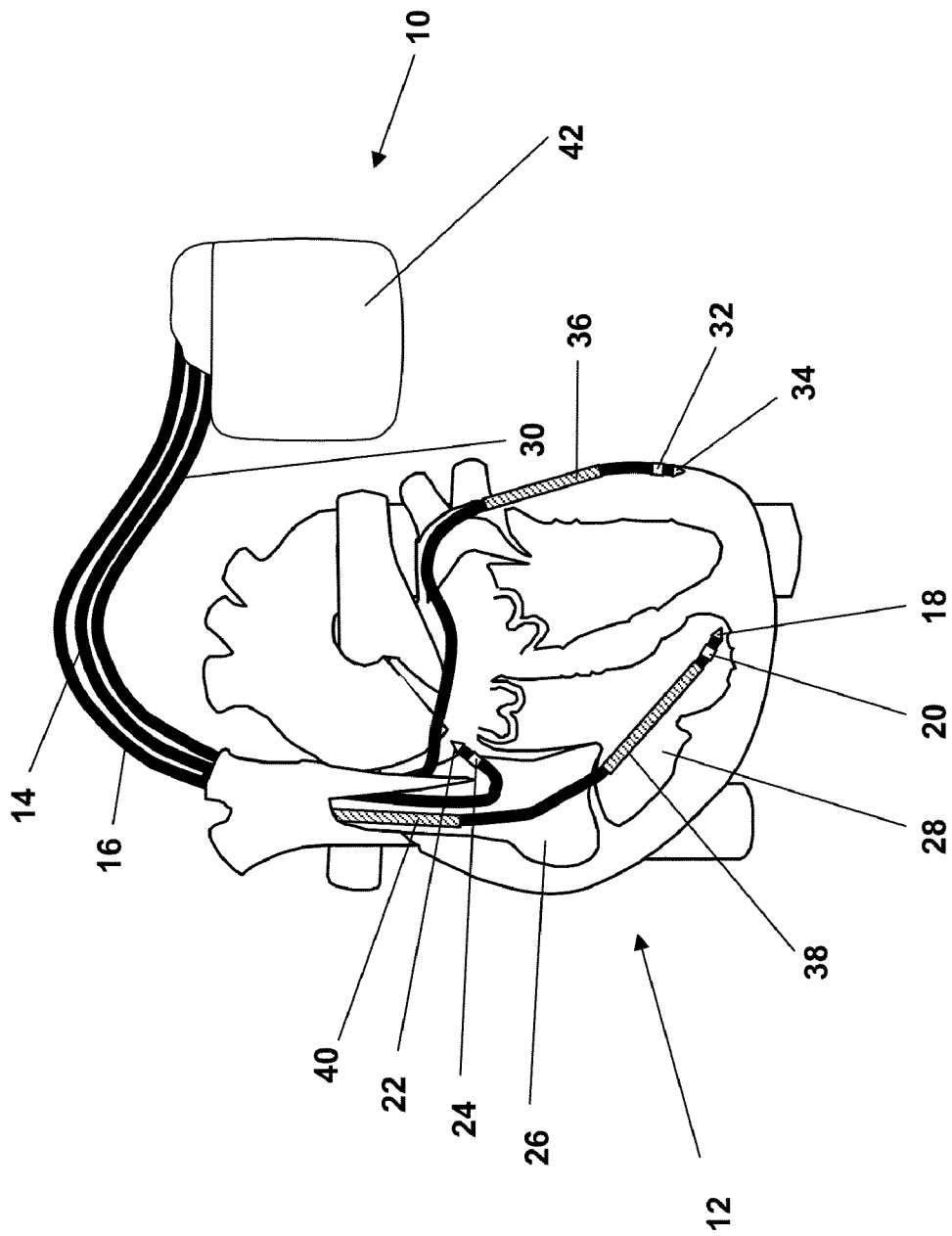
FIG. 1 shows an implantable medical device including a monitoring device connected to leads placed in a heart.

In FIG. 1 an implantable medical device, a three chamber biventricular pacemaker and cardioverter/defibrillator 10 that is connected to pacing/sensing leads placed in a heart 12 is illustrated. Implantable medical device 10 incorporates a monitoring device.

The implantable medical device 10 is electrically coupled to heart 12 by way of leads 14, 16 and 30.

Lead 14 is a right atrial electrode lead that has a pair of right atrial electrodes 22 and 24 that are in contact with the right atrium 26 of the heart 12.

Lead 16 is a right ventricular electrode lead that has a pair of ventricular stimulation and sensing electrodes 18 and 20 that are in contact with the right ventricle 28 of heart 12. Further, a ventricular defibrillation shock coil 38 and an atrial defibrillation shock coil 40 are arranged on lead 16.

Electrodes 22 and 18 are tip electrodes at the very distal end of leads 14 and 16, respectively. Electrode 22 is a right atrial tip electrode RA Tip and electrode 18 is a right ventricular tip electrode RV Tip. Electrodes 24 and 20 are ring electrodes in close proximity but electrically isolated from the respective tip electrodes 22 and 18. Electrode 24 forms a right atrial ring electrode RA Ring and electrode 20 forms a right ventricular ring electrode RV Ring. Ventricular defibrillation shock coil 38 and atrial defibrillation shock coil 40 are coil electrodes providing a relatively large surface area when compared to the electrodes 18, 22, 20 and 24.

Lead 30 is a left ventricular electrode lead passing through the coronary sinus of heart 12 and having a left ventricular ring electrode LV Ring 32, and a left ventricular tip electrode LV Tip 34. Further, a left ventricular defibrillation shock coil 36 is arranged on lead 30.

Implantable medical device 10 has a case 42 made from electrically conductive material such as titanium that can serve as a large surface electrode herein called "can".

The plurality of electrodes 18, 20, 22, 24, 32, 34, 36, 38 and 40 connected to implantable medical device 10 together with case 42 allow for a number of different electrode configurations for measuring intrathoracic and intracardiac impedance.

Figure 3:
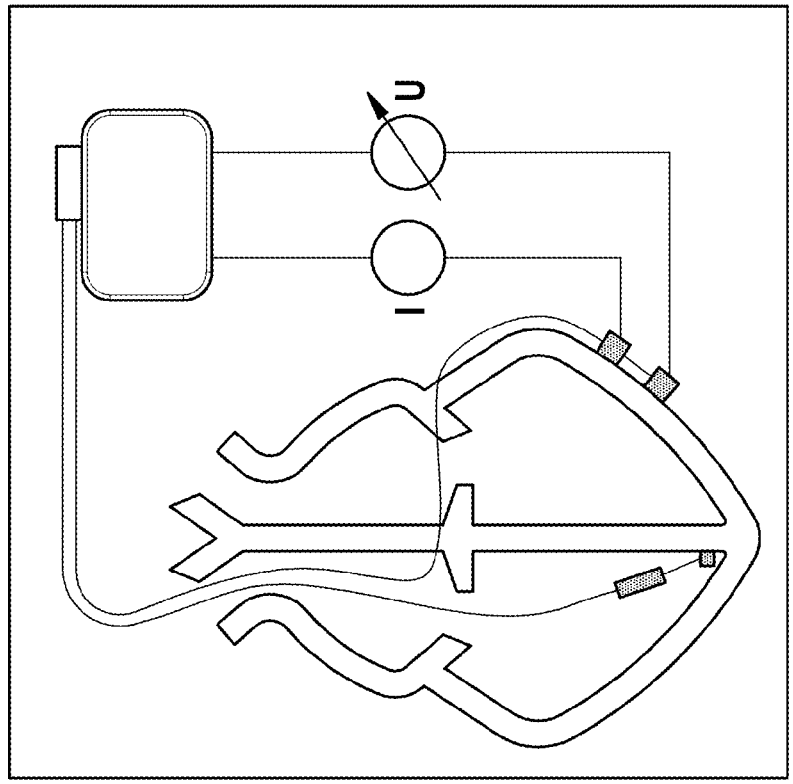
FIG. 3 shows two representative electrode configurations for intrathoracic impedance measurement.
Figure 3:
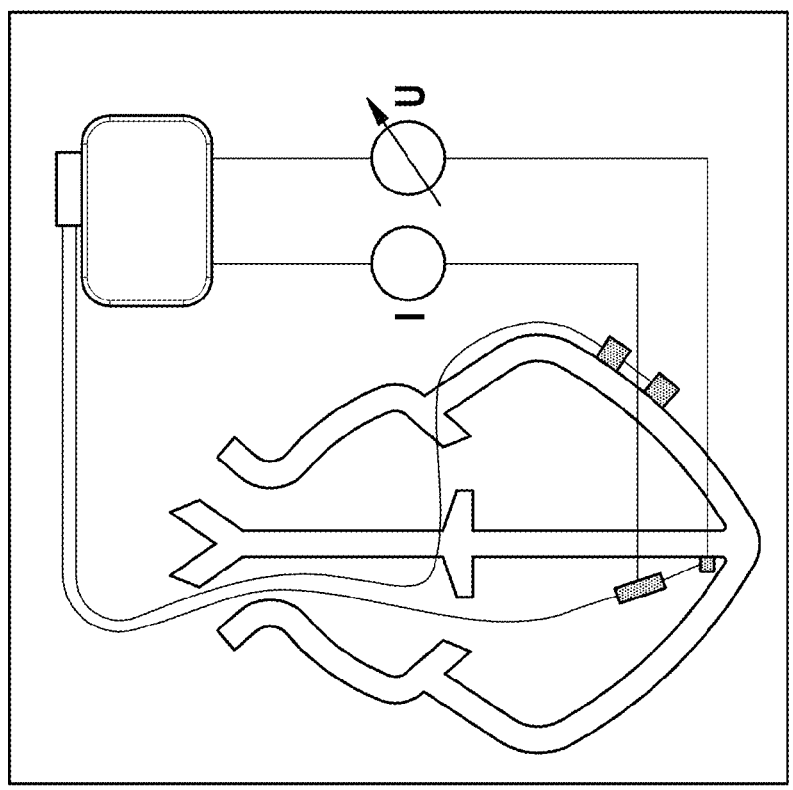

A subset of configurations possible with the device in FIG. 1, are the preferred configurations illustrated conceptually in FIG. 3.

Figure 2:
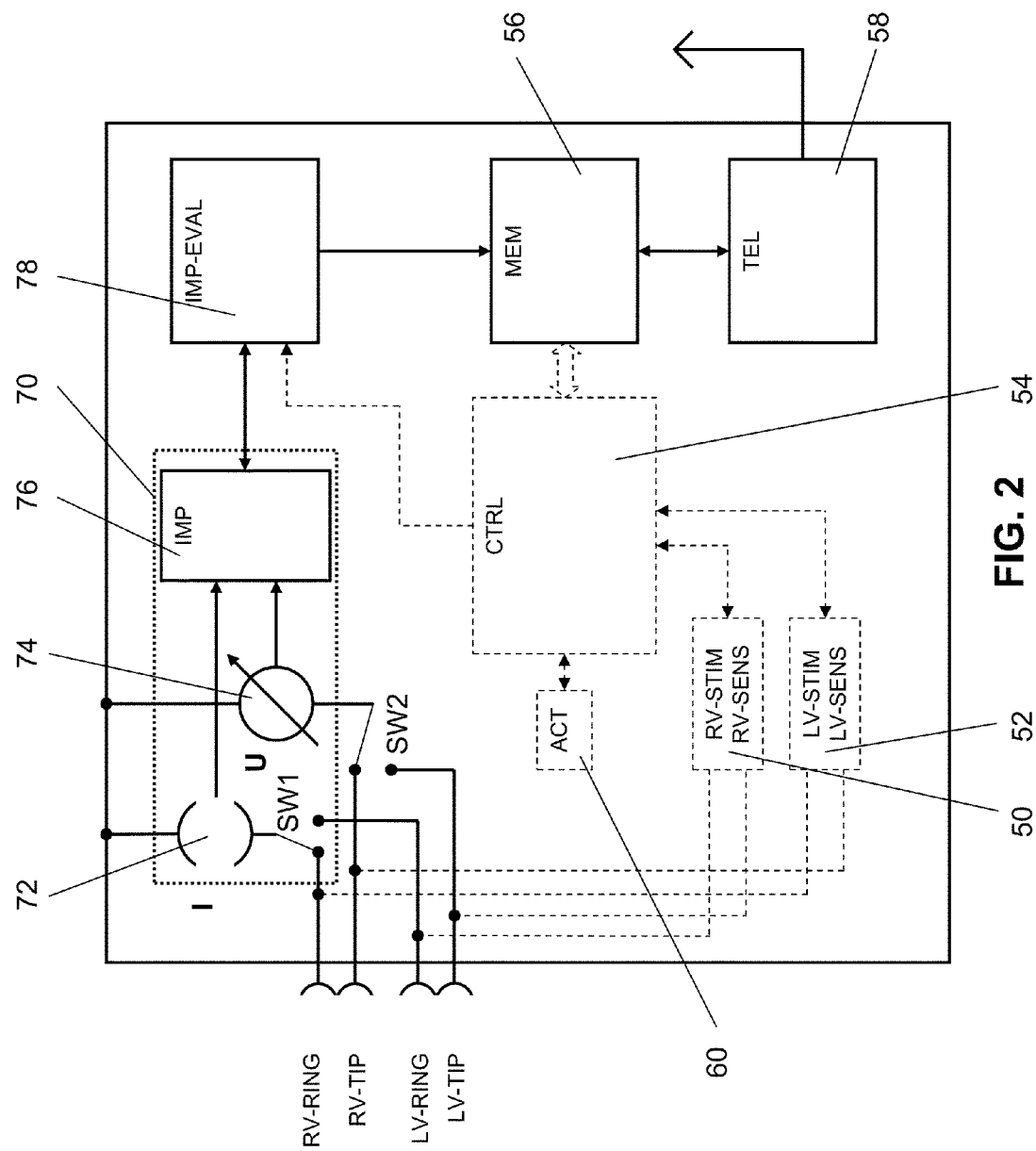
FIG. 2 is a schematic block diagram of one configuration of the device of FIG. 1. For simplicity, the atrial sensing and stimulation channels are omitted.

FIG. 2 illustrates a simplified block diagram of an implantable medical device, for example, the one shown as item 10 in FIG. 1. While FIG. 1 shows a three chamber biventricular pacemaker and cardioverter/defibrillator, in FIG. 2 no means for connecting atrial electrodes or shock electrodes and means for driving these electrodes are shown. However, such means may be provided as is known in the art.

During operation of the implantable medical device leads 16 and 30 (of FIG. 1) are connected to respective output/input terminals RV RING, RV TIP, LV RING and LV TIP, items 20, 18, 32, and 34, respectively, of implantable medical device 10 as indicated in FIG. 1. For pacing the right and the left ventricle they carry stimulating pulses to the tip electrodes 18 and 34 from a right ventricular stimulation pulse generator RV STIM 50 and a left ventricular stimulation pulse generator LV STIM 52, respectively. Further, electrical signals from the right ventricle are carried from the electrode pair 18 and 20, through the lead 16, to the input terminal of right ventricular sensing stage RV SENS 50; and electrical signals from the left ventricle are carried from the electrode pair 32 and 34, through the lead 30, to the input terminal of a left ventricular sensing stage LV SENS 52.

Controlling the implantable medical device 10 is a control unit CTRL 54 that is connected to stimulation pulse generators/sensing stages RV STIM/RV SENS 50 and LV STIM/LV SENS 52.

Control unit CTRL 54 receives the output signals from the right ventricular sensing stage RV SENS 50 and from the left ventricular sensing stage LV SENS 52. The output signals of sensing stages RV SENS 50 and LV SENS 52 are generated each time an R wave representing an intrinsic ventricular event in the respective ventricle is sensed within the heart 12. Thus, control unit is capable of detecting excitations of the myocardium indicating a ventricular contraction and to act as a heart rate detector for determination of a heart rate.

Control unit CTRL 54 also generates trigger signals that are sent to the right ventricular stimulation pulse generator RV STIM 50 and the left ventricular stimulation pulse generator LV STIM 52, respectively. Control unit CTRL 54 comprises circuitry for timing ventricular stimulation pulses (atrial stimulation pulses are also possible but not shown in FIG. 2) according to an adequate stimulation rate that can be adapted to a patient's hemodynamic need as pointed out below.

Still referring to FIG. 2, the implantable medical device 10 includes a memory circuit MEM 56 that is coupled to the control unit CTRL 54 over a suitable data/address bus. This memory circuit MEM 56 allows certain control parameters, used by the control unit CTRL 54 in controlling the operation of the implantable medical device 10, to be programmable, stored and modified, as required, in order to customize the implantable medical device's operation to suit the needs of a particular patient. Such data includes basic timing intervals used during operation of the implantable medical device 10 for triggering of ventricular or atrial stimulation pulses.

Further, data sensed during the operation of the implantable medical device may be stored in the memory MEM 56 for later retrieval and analysis.

For impedance measurement, an impedance measurement unit 70 is provided. Impedance measurement unit 70 comprises a constant current source 72 and a voltage measurement unit 74 that are respectively connected or can be connected to electrodes for intracorporeal placement as shown in FIG. 1. In order to allow for a plurality of impedance measurement electrode configurations, preferably some means of switching is provided between the constant current source 72 and the electrode terminals of the implantable medical device 10. In FIG. 2 switches SW1 and SW2 are shown.

As an alternative to constant current source 72 a constant voltage source can be provided. Then, the measuring unit will be adapted to measure a current strength of a current fed through a body by said constant voltage source.

Both, constant current source 72 and measuring unit 74, are connected to an impedance value determination unit 76 that is adapted to determine an impedance value for each measuring current pulse delivered by the constant current source 72.

Further, an impedance evaluation unit 78 is provided, that is connected to said impedance determination unit 76 and that is adapted to control said impedance determination unit and to evaluate a sequence of consecutive impedance values determined by said impedance measurement unit 70. Impedance evaluation unit 78 is also connected to memory 56 for storing of impedance data. Impedance measurement unit 70 and impedance evaluation unit can be controlled by control unit CTRL 54.

The impedance measurement unit 70 is adapted to determine at least transthoracic impedance values and preferably in addition intracardiac impedance values for same period of time, wherein the intracardiac impedance values are preferably sampled with a higher sampling rate than the transthoracic impedance values.

A telemetry circuit TEL 58 is further included in the implantable medical device 10. This telemetry circuit TEL 58 is connected to the control unit CTRL 54 and memory MEM 56 by way of a suitable command/data bus. Telemetry circuit TEL 58 allows for wireless data exchange between the implantable medical device 10 and some remote programming or analyzing device, which can be part of a centralized service center serving multiple implantable medical devices.

Implantable medical device 10 usually comprises an activity sensor ACT 60 that is used for rate adaptation and can be of further use for evaluation of impedance values and therefore is connected to the impedance evaluation unit 78 via control unit CTRL 54. In particular, an output signal by activity sensor 60 is used by impedance evaluation 78 to derive and recognize periods of physical activity and periods of rest. This information is used for further processing and trending of the information derived from the impedance signal.

Monitoring the heart failure status is accomplished by the impedance evaluation unit 78 by trending analysis of multiple physiological parameters of the patient, including at least the diurnal pattern of the respiration rate, which is measured by means of transthoracic impedance of the implantable cardiac device.

In one typical embodiment, early detection of heart failure decompensation is made when the implantable cardiac device detects an increase of the night respiration rate of the patient, and/or decrease of the daytime respiration rate of the patient, and/or decrease of the circadian variability of the respiration rate of the patient. Alternatively, heart failure monitoring is achieved by trending analysis of multiple physiological parameters, including but not limited to, the respiration rate, the heart rate, and the heart rate variability.

According to this invention, the implantable cardiac device continuously measures the transthoracic impedance signal to derive the patient's respiration rate. As is well known in the art, there are different means to measure the transthoracic impedance signal by choosing various electrode configurations for current injection and voltage measurement. Typically, the impedance vectors pass through the lung in order to detect the respiration activity. FIG. 3 shows two representative tripolar configurations for such impedance measurement.

Further configurations and preferred details for impedance measurement are disclosed in US2008/0300504 incorporated herein by reference.

In the left panel of FIG. 3, the current is injected between the right ventricular ring and can, and the voltage is measured between the right ventricular tip and can. In the right panel of FIG. 3, the current is injected between the left ventricular ring and can, and the voltage is measured between the left ventricular tip and can.

Impedance value determination unit 76 calculates the transthoracic impedance as the ratio between the measured voltage and the injected current. In a preferred embodiment, the impedance signal is measured with sampling frequency of at least 8 Hz.

Impedance evaluation unit 78 further processes the impedance signal to remove a high frequency cardiac component, e.g., by using a low-pass filter with corner frequency of 2.5 Hz, to thus obtain the low frequency respiratory component. Impedance evaluation unit 78 further determines the peak-to-peak interval of the resulting respiration component of the transthoracic impedance signal, or the respiration cycle length. Its inverse, or the number of respiration cycles within a predefined time interval (e.g., one minute), is the respiration rate. In an alternative embodiment the inflection at the end of expiration to begin inspiration is identified to determine the respiration cycle length.

Figure 4:
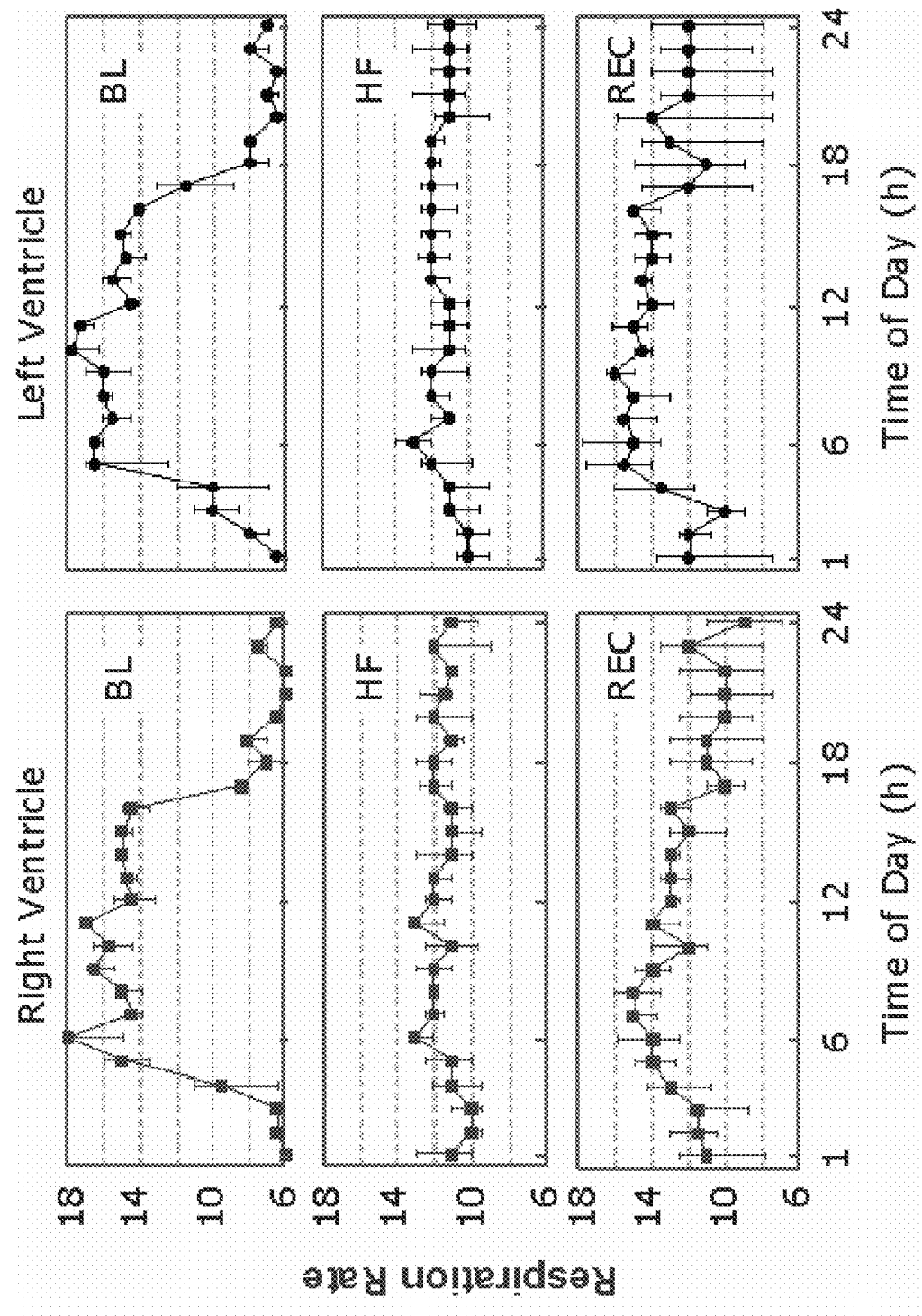
FIG. 4 illustrates the circadian patterns of the respiration rate measured in a chronic animal study.

FIG. 4 illustrates the circadian patterns of the respiration rate measured in a chronic animal study. In this study, 10 mature Yucatan minipigs were chronically instrumented with a biventricular pacemaker and a left ventricular pressure-measuring device. For each animal, after a recovery and stabilization period following device implantation, heart failure was inducted by using high rate right ventricular pacing at 240 ppm over 2-4 weeks. Hourly left ventricular pressure measurements and weekly echo data were used to monitor the development of heart failure. Hourly recording of right ventricular and left ventricular tripolar impedance (during intrinsic rhythm) was performed over the course of the study, including 2-4 weeks after cessation of high rate pacing (recovery period). Respiratory measurements of respiration rate, tidal amplitude, and minute ventilation were extracted hourly from the tripolar impedance measurements.

Still refer to FIG. 4. In all panels, the x-axis is the hour of the day, and the y-axis is the respiration rate (unit: cycles/minute) measured by the implantable cardiac device. The plotted respiration rate data are averaged over 10 subjects. The left panels show the respiration rate derived from the right ventricular tripolar impedance data obtained using the configuration shown in the left panel of FIG. 3, and the right panels show the respiration rate derived from the left ventricular impedance data obtained using the configuration shown in the right panel of FIG. 3.

The top panels show the 24-hour respiration rate during the baseline period (BL) (before heart failure induction). The respiration rate shows clear circadian variation that increases during the daytime whereas it decreases during the night time. The middle panels show the 24-hour respiration rate during the period with confirmed heart failure (HF) status. Clearly, the circadian variation of the respiration rate is dramatically reduced, evidenced by decreased respiration rate in the daytime and elevated respiration rate in the night time. The bottom panels show the 24-hour respiration rate during the recovery period (REC) (after stopping high rate pacing). Evidently, the circadian pattern of the respiration rate also recovered to some extent, although not to the baseline level (prior to heart failure induction).

It is believed by the inventors that the patient's respiration rate contains important diagnostic information on heart failure status, which is independent from other physiological parameters such as heart rate and heart rate variability. Normal function of the physiological system requires balance of the autonomic nervous system (ANS). However, in heart failure patients the sympathetic tone is increased whereas the parasympathetic tone is suppressed. Consequently, this results in increase of resting respiration rate, increase in resting heart rate, and decrease of the hear rate variability.

According to this invention, the night respiration rate is a reasonable measure of the resting respiration rate, thus elevation of the night respiration rate is a strong indicator of worsening heart failure. The nighttime respiration is less subject to the interference of a conscious subject and environmental stimuli, and thus reflects more autonomic driven respiration. It is also believed by the inventors that the daytime respiration rate also contains prognostic information on patient's heart failure status, because reduced daytime respiration rate likely reflects decreased daytime activity level, which is associated with worsening heart failure. Consequently, the damped circadian variation of the respiration rate (reduced difference between daytime and night time respiration rates) is also a strong indicator of worsening heart failure.

In a preferred embodiment, a pacemaker, implantable cardioverter/defibrillator (ICD), or cardiac resynchronization therapy (CRT) device with configurable impedance circuits is used to measure the tripolar intrathoracic impedance signal as illustrated in FIG. 3.

Methods for monitoring heart failure status by processing a transthoracic impedance signal are illustrated hereinafter. These methods can be carried out by the impedance evaluation unit 78 or by other means including a remote service center.

Then, from the transthoracic impedance signal, the cardiac component is separated from the respiration component. In a predefined time interval e.g. hourly, the respiration cycle length and/or the respiration rate is measured from the respiration component. Measured values (time interval, respiration cycle length and/or respiration rate) are stored in memory 56 for further processing.

The processing (to be carried out by the impedance evaluation unit 78) comprises:

calculation of overall statistics of the measured respiration rate, e.g. moving average within the past x-hours.

Calculation of separate day and night statistics of the measured respiration rate with user-programmable daytime and night time settings, e.g. daytime between 10 am and 5 pm, and night time between 1 am and 5 am.

Data may be transmitted routinely (daily) and as necessary (alert) via telemetry unit 58 to one or all of a remote server, data base and expert system using well known data transmission technologies for further processing e.g. for heart failure assessment.

Change from a baseline state of heart function to a worsening state, will be characterized by an increase of the night respiration rate, and/or decrease of the day-time respiration rate, and/or decrease of the circadian variability of the respiration rate of the patient. Alert for worsening heart failure is generated when the increase or decrease of the above parameters crosses a predefined threshold value or percentage as compared to the baseline.

Alternatively, a composite score (CS) is constructed from multiple physiological parameters. For example, define $CS=a*rRR+b/dRR+c*rHR+d/HRV$, where CS is the composite score, a, b, c, and d are predefined non-positive coefficients (weighting factors), rRR is the resting (night) respiration rate, dRR is the difference between day and night respiration rates (or alternatively, an index of 24-hour respiration rate variability), rHR is the resting (night) heart rate, and heart rate variability (HRV) is an index of 24-hour heart rate variability as known in the art. Worsening heart failure is indicated by increase of rRR, increase of rHR, decrease of dRR, and decrease of heart rate variability (HRV). Thus, early detection of heart failure decompensation is made when CS is increased above a predefined threshold. It should be understood that other definitions of CS can also be made based on the same concept.

What is claimed is:

1. A monitoring device for monitoring and analyzing physiological signals comprising:

a transthoracic impedance measurement unit;

an evaluation unit connected to said transthoracic impedance measurement unit;

said transthoracic impedance measurement unit configured to conduct a transthoracic impedance measurement and to generate a transthoracic impedance signal that represents a measured transthoracic impedance at consecutive points in time;

said evaluation unit configured to process said transthoracic impedance signal received from said transthoracic impedance measurement unit and to thus generate a respiration signal and to generate therefrom an evaluation signal that reflects at least a diurnal pattern of a respiration rate;

a sensing unit configured to process an EGM signal that represents intracardiac myocardial electric potentials and determine therefrom a heart rate signal;

wherein said evaluation unit is configured to perform a trending analysis of multiple different physiological parameters, comprising a heart rate, a heart rate variability and said respiratory rate;

wherein said evaluation unit is configured to determine overall statistics of a respiration rate signal; and, wherein said evaluation unit is configured to determine a composite score from said multiple different physiological parameters; wherein said evaluation unit is configured to determine said composite score as follows:

$$CS = a*rRR + b/dRR + c*rHR + d/HRV,$$

where a, b, c, and d are predefined non-negative coefficients, rRR is a resting respiration rate, dRR is a difference between day and night respiration rates, rHR is a resting heart rate, and HRV is an index of 24-hour heart rate variability.

2. The monitoring device of claim 1 wherein said evaluation unit is configured to detect an increase of a night respiration rate of a patient, and/or decrease of a daytime respiration rate of the patient, and/or decrease of a circadian variability of the respiration rate and to generate an alert signal upon detection of one or more of said increases or decreases.

3. The monitoring device of claim 1 further comprising:
a metal can;
wherein said transthoracic impedance measurement unit is connected or can be connected to a bipolar ventricular electrode lead having a tip electrode at its distal end and a ring electrode close to said tip electrode; and,
wherein said transthoracic impedance measurement unit is configured to inject a current between said ring electrode and said metal can, and to measure a voltage between said tip electrode and said metal can.

4. The monitoring device of claim 3 wherein said transthoracic impedance measurement unit is configured to calculate an impedance as a ratio between a measured voltage and an injected current.

5. The monitoring device of claim 3 wherein said transthoracic impedance measurement unit is configured to measure an impedance signal with a sampling frequency of at least 8 Hz.

6. The monitoring device of claim 3 wherein said transthoracic impedance measurement unit comprises:
a constant current source or a constant voltage source having current feed terminals that are connected or can be connected to electrodes for intracorporal placement and that is configured to generate measuring current pulses having a constant current strength or a constant voltage, respectively, configured to cause the current to be fed through a body via intracorporally placed electrodes;
a measuring unit configured to measure a voltage that corresponds to the current fed through the body by said constant current source or a current strength of the current fed through the body by said constant voltage source, respectively, to determine an impedance value for each measuring current pulse; and,
an impedance value determination unit that is connected to said constant current source or said constant voltage source and the measuring unit.

7. The monitoring device of claim 1 further comprising a low-pass filter and wherein said evaluation unit is configured to process an impedance signal to remove high frequency cardiac components with the low-pass filter, to obtain the respiration signal.

8. The monitoring device of claim 1 wherein said evaluation unit is configured to process an impedance signal to determine a peak-to-peak interval of the respiration signal derived from an intrathoracic impedance signal that is a respiration cycle length.

9. The monitoring device of claim 1 wherein said evaluation unit is configured to process an impedance signal to determine an inflection at an end of expiration and a start of inspiration to determine a respiration cycle length of the respiration signal derived from an intrathoracic impedance signal.

10. The monitoring device of claim 1 further comprising a memory that is configured to store signals and/or data generated by said evaluation unit to further process.

11. The monitoring device of claim 10 further comprising a telemetry unit that is configured for wireless transmission of data, wherein said monitoring device is configured to routinely transmit signals and/or data generated by said evaluation unit to a remote server.

12. The monitoring device of claim 1 wherein said evaluation unit is configured to determine separate day and night statistics of a measured respiration rate with user-programmable daytime and night time settings.

13. The monitoring device of claim 1 where dRR is an index of 24-hour respiration rate variability.

14. The monitoring device of claim 1 wherein said evaluation unit is configured to generate an alert signal if the composite score exceeds a predefined threshold value, due to either an increase of rRR, or an increase of rHR, or a decrease of dRR, or a decrease of HRV, or their combinations.

15. A monitoring device for monitoring and analyzing physiological signals comprising:
a transthoracic impedance measurement unit;
an evaluation unit connected to said transthoracic impedance measurement unit;
said transthoracic impedance measurement unit configured to conduct a transthoracic impedance measurement and to generate a transthoracic impedance signal that represents a measured transthoracic impedance at consecutive points in time;
said evaluation unit configured to process said transthoracic impedance signal received from said transthoracic impedance measurement unit and to thus generate a respiration signal and to generate therefrom an evaluation signal that reflects at least a diurnal pattern of a respiration rate;
wherein said evaluation unit is configured to determine a composite score from multiple different physiological parameters; and, wherein said evaluation unit is configured to determine said composite score as follows:

$$CS = a*rRR + b/dRR + c*rHR + d/HRV,$$

where a, b, c, and d are predefined non-negative coefficients, rRR is a resting respiration rate, dRR is a difference between day and night respiration rates, rHR is a resting heart rate, and HRV is an index of 24-hour heart rate variability.

* * * * *